United States Patent
Jameson et al.

(10) Patent No.: US 11,796,532 B2
(45) Date of Patent: Oct. 24, 2023

(54) BREATH SENSOR APPARATUS AND METHODS OF USE

(71) Applicant: Carrot, Inc., Redwood City, CA (US)

(72) Inventors: Allen Jameson, Sunnyvale, CA (US); David S. Utley, Redwood City, CA (US)

(73) Assignee: Pivot Health Technologies Inc., San Carlos, CA (US)

(*) Notice: Subject to any disclaimer, the term of this patent is extended or adjusted under 35 U.S.C. 154(b) by 0 days.

(21) Appl. No.: 17/456,070

(22) Filed: Nov. 22, 2021

(65) Prior Publication Data

US 2022/0082550 A1    Mar. 17, 2022

Related U.S. Application Data

(62) Division of application No. 15/782,718, filed on Oct. 12, 2017, now Pat. No. 11,209,417.

(51) Int. Cl.
*G01N 33/497* (2006.01)
*G01N 33/00* (2006.01)

(52) U.S. Cl.
CPC ......... *G01N 33/497* (2013.01); *G01N 33/004* (2013.01); *G01N 33/005* (2013.01); *G01N 33/0006* (2013.01); *G01N 33/0014* (2013.01); *G01N 33/0016* (2013.01)

(58) Field of Classification Search
CPC ............. G01N 33/497; G01N 33/0006; G01N 33/0014; G01N 33/0016; G01N 33/004; G01N 33/005; A61B 5/0002; A61B 5/0803; A61B 5/082; A61B 5/097
USPC ........................................................ 73/23.3
See application file for complete search history.

(56) References Cited

U.S. PATENT DOCUMENTS

| | | | |
|---|---|---|---|
| 4,633,704 A | 1/1987 | Tantram et al. | |
| 6,443,908 B2 * | 9/2002 | Stone | A61B 5/0836 600/532 |
| 6,479,019 B1 | 11/2002 | Goldstein et al. | |
| 6,840,084 B2 | 1/2005 | Nikolskaya | |
| 8,266,795 B2 | 9/2012 | Wagner | |
| 9,709,582 B1 * | 7/2017 | Gordon | G01N 33/582 |
| 10,499,819 B2 | 12/2019 | Wondka et al. | |
| 10,861,595 B2 | 12/2020 | Satake et al. | |
| 10,923,220 B2 | 2/2021 | Satake | |
| 2001/0049477 A1 | 12/2001 | Stone | |
| 2005/0083527 A1 | 4/2005 | Flaherty et al. | |
| 2006/0266353 A1 | 11/2006 | Yamada et al. | |

(Continued)

FOREIGN PATENT DOCUMENTS

| | | | | |
|---|---|---|---|---|
| CA | 2736243 A1 * | 3/2010 | ........... | C12Q 1/6851 |
| WO | WO 2010/005738 | 1/2010 | | |

(Continued)

*Primary Examiner* — Marrit Eyassu
(74) *Attorney, Agent, or Firm* — Levine Bagade Han LLP

(57) ABSTRACT

Breath sensor apparatus and methods of use are described herein where a flow control apparatus may generally comprise a sampling chamber defining a volume and one or more openings into the sampling chamber, at least one sensor in fluid communication with the sampling chamber, wherein the at least one sensor is configured to detect the analyte. The sampling chamber may also be configured to receive the breath sample into the sampling chamber and into contact with the at least one sensor via diffusion into the sampling chamber.

9 Claims, 13 Drawing Sheets

(56) References Cited

U.S. PATENT DOCUMENTS

| | | |
|---|---|---|
| 2008/0114223 A1 | 5/2008 | Pierry et al. |
| 2012/0266654 A1 | 10/2012 | Chiarugi et al. |
| 2012/0310104 A1 | 12/2012 | Van Kesteren et al. |
| 2014/0275857 A1 | 9/2014 | Toth et al. |
| 2014/0358019 A1 | 12/2014 | Johnson |
| 2015/0105684 A1 | 4/2015 | Yano et al. |
| 2015/0201865 A1* | 7/2015 | Forzani ................ G01N 33/497 600/532 |
| 2015/0260706 A1 | 9/2015 | Killard et al. |
| 2015/0265184 A1 | 9/2015 | Wondka et al. |
| 2015/0362478 A1 | 12/2015 | Phillips |
| 2016/0073930 A1 | 3/2016 | Stetter et al. |
| 2016/0084861 A1* | 3/2016 | Kleider ............ G01N 35/00693 422/68.1 |
| 2017/0055875 A1 | 3/2017 | Candell et al. |
| 2017/0074844 A1 | 3/2017 | Tolmie et al. |
| 2017/0119279 A1 | 5/2017 | Ahmad et al. |
| 2017/0176411 A1 | 6/2017 | Trainor et al. |
| 2017/0191984 A1* | 7/2017 | Ma ....................... A61B 5/0836 |
| 2017/0265778 A1 | 9/2017 | Reichlyn et al. |
| 2018/0271403 A1 | 9/2018 | Furusaki et al. |
| 2019/0017996 A1 | 1/2019 | Chou et al. |
| 2019/0113501 A1 | 4/2019 | Jameson et al. |
| 2019/0261891 A1 | 8/2019 | Ahmad et al. |
| 2019/0344281 A1 | 11/2019 | Ahmad et al. |
| 2020/0305729 A1 | 10/2020 | Wondka et al. |
| 2021/0057066 A1 | 2/2021 | Satake et al. |
| 2021/0196148 A1 | 7/2021 | Jameson et al. |
| 2021/0204834 A1 | 7/2021 | Jameson et al. |

FOREIGN PATENT DOCUMENTS

| | | |
|---|---|---|
| WO | WO 2019/074666 | 4/2019 |
| WO | WO 2021/138197 | 7/2021 |

* cited by examiner

BREATH SENSOR APPARATUS AND METHODS OF USE

CROSS-REFERENCE TO RELATED APPLICATIONS

This application is a divisional of U.S. patent application Ser. No. 15/782,718 filed Oct. 12, 2017 (now U.S. Pat. No. 11,209,417), which is incorporated herein by reference in its entirety.

FIELD OF THE INVENTION

The present invention relates to apparatus and methods for receiving and detecting biological parameters from breath samples. In particular, the present invention relates to apparatus and methods of use for receiving and detecting biological parameters from breath samples exhaled from a subject and into a portable breath sensor apparatus.

BACKGROUND OF THE INVENTION

The health problems associated with tobacco smoking are well known. Cigarette smoke contains nicotine as well as many other chemical compounds and additives. Tobacco smoke exposes an individual to carbon monoxide as well as these other compounds, many of which are carcinogenic and toxic to the smoker and those around the smoker. The presence and level of carbon monoxide in the exhaled breath of the smoker can provide a marker for identifying the overall smoking behavior of that individual as well as provide a marker for their overall exposure to the other toxic compounds.

In order to sample the exhaled breath, a portable breath sensor which is readily carried by the user and which is unobtrusive is desirable. However, the relatively reduced size of the breath sensor also brings a number of challenges in capturing and accurately measuring samples of the exhaled breath. Factors such as moisture content in the breath as well as breath temperature may affect the accuracy of the sensors used to measure the parameters due to the relatively small size.

There remains a need for a breath sensor which is able to sample and accurately detect parameters from exhaled breath while being readily portable.

SUMMARY OF THE INVENTION

Personal sampling unit may generally comprise a housing having a shape which allows for the user to hold and manipulate the unit with a single hand. The housing may incorporate the input trigger as well as one or more indicators such as indicator. The collection tube may be comprised of a tube defining a lumen and which extends from the housing. Within the housing, a first sensor and second sensor which in turn may be mounted upon a substrate such as a printed circuit board. Although in other variations, one or more sensors may be used depending upon the parameters being detected. A power port and/or data access port may also be integrated with the printed circuit board and readily accessible by a remote device such as a computer, server, smartphone, or other device. The sensors may include any number of different sensor types including chemical gas sensors, electrochemical gas sensors, etc. for detecting agents such as carbon monoxide in the case of detecting smoking related inhalation.

When detecting agents from breath samples from a subject, it is generally desirable to avoid temperature and humidity impacts on the sensors particularly in breath sensing devices which are compact as temperature swings and humidity may interfere with the detected signals in the sensors. Larger breath sensing devices are able to readily contend with temperature and humidity variances due to their relatively larger mass and longer flow paths as the sampled breath temperature is reduced and moisture is removed prior to the breath sample reaching the sensor.

One variation of a flow control apparatus for measuring an analyte from a breath sample of a subject may generally comprise a sampling chamber defining a volume and one or more openings into the sampling chamber, at least one sensor in fluid communication with the sampling chamber, wherein the at least one sensor is configured to detect the analyte, and wherein the sampling chamber is configured to receive the breath sample into the sampling chamber and into contact with the at least one sensor via diffusion into the sampling chamber.

Another variation of a flow apparatus for measuring a concentration of an analyte of interest from an individual's breath may generally comprise a sampling chamber including at least one opening to receive a portion of the breath, wherein a remainder of the breath is diverted and vented, at least one sensor positioned in fluid communication with the sampling chamber, wherein the at least one sensor is configured to detect the analyte of interest, and wherein the sampling chamber is configured such that a majority of the portion of the breath in contact with the sensor is introduced via diffusion, rather than flow, into the sampling chamber.

One variation of a method of extrapolating a final value of a parameter from a breath sample may generally comprise obtaining a calibration curve of a gas having a known parameter concentration, recording at least a portion of the calibration curve as a function of time, measuring an input response curve of the parameter from the breath sample over a period of time, associating the input response curve to the calibration curve, and extrapolating the final value of the parameter from the breath sample based on the calibration curve associated with the input response curve.

Another variation of a flow control assembly may generally comprise a proximal receiving channel sized to receive a fluid sample, a dispersion channel fluidly connected to the proximal receiving channel, a main receiving channel, wherein the dispersion channel is configured to divert a portion of the fluid sample to the main receiving channel and a majority of the fluid sample to one or more secondary channels for venting from the assembly, and one or more sampling chambers fluidly connected to the main receiving channel via one or more openings.

Another method of measuring a fluid sample may generally comprise receiving the fluid sample within a proximal receiving channel, diverting a majority of the fluid sample to one or more secondary channels, diverting a portion of the fluid sample into a main receiving channel, and introducing the portion of the fluid sample into contact with one or more sensors for determining a parameter from the fluid sample.

In order for a relatively smaller device such as the personal sampling unit described herein to accurately detect breath samples, one or several mechanisms may be employed to filter out moisture from the breath sample as well as reduce its temperature. A flow control assembly may be incorporated into the housing for controlling the flow of a breath sample to the sensors. The assembly may have a receiving channel into which the collection tube may be inserted and retained. The lumen of the collection tube may be fluidly connected through the receiving channel and into a dispersion channel which extends into and is fluidly coupled to one or more secondary channels which define corresponding second fluid pathways extending away from the dispersion channel, e.g., at an angle relative to the dispersion channel.

One or more primary channels may further extend away from and fluid coupled with the dispersion channel so that the primary channels open into a receiving channel which is defined by a barrier formed around the receiving channel. The dispersion channel helps to divert a majority of the sampled breath into the secondary channels so that a relatively smaller portion of the breath passes through the primary channels and into the receiving channel. For instance, about 80% of the breath sample may be diverted into the secondary channels where it may then be vented out from of the housing. The remaining, e.g., 20% of the breath sample, may then enter into the receiving channel so that the diverted flow helps to decrease the moisture level in the sampled breath. In other variations, more than 50% of the breath sample may be diverted so that less than 50% of the breath sample enters into the receiving channel. Additionally, the relatively larger volume defined by the receiving channel may further help to reduce the temperature of the sampled breath.

The openings extending into the respective first and second sampling chambers are sized to be relatively smaller and may number from a single opening to multiple openings which help to further maintain the flow rate of the sampled breath entering the sampling chambers to a minimum flow rate of, e.g., about 4 mL/sec.

Contained within the first and second sampling chambers are respective first and second filters which further help to remove any additional moisture from the sampled breath. Additionally, respective first and second seals may surround the sampling chambers to contain the sampled breath over the sensors for detection. These first and second filters help to diffuse the flow path through a matrix, e.g., porous material, which not only removes moisture but also helps to further reduce the temperature of the sampled breath due to their additional thermal mass. The filters may be comprised of various materials that also filter out various chemicals such as alcohols, sulfur compounds, carbon monoxide, etc.

Another variation for reducing moisture and cooling the sampled breath may include incorporating a tortuous flow path which increases the surface area in contact with the sampled breath. This may include a coiled path or a maze which helps to drop the temperature and further allows for moisture to condense out of the breath and onto the surface area. In yet another variation, rather than utilizing barriers or baffles to create a tortuous flow path, tubing may be used for flowing the breath sample.

Alternatively, moisture may be removed from the sample by utilizing, e.g., a moisture-permeable membrane along the flow path or a hygroscopic material such as silica that may absorb the moisture from the sample. In these variations where moisture is condensed or absorbed along the flow path, the condensed water is desirably removed from the flow assembly. Removal may be accomplished in one variation by increasing a number of vent holes from the flow path to the environment while in another variation, a water transport membrane, e.g., Nafion or another water-permeable solid, may be used to transport the water away from the flow assembly.

In yet another variation, an active mechanism such as a pump may be used to draw a portion of the sample from the flow path after the initial exhalation from the subject is introduced into the unit.

Once the breath sample has been introduced through the openings and past the filter, the sample may be introduced within a sensing chamber contained within an interior of the sampling chamber where it comes into contact with the sensor. The surface of the sensor generally presents a planar face against which a contact region of the sampling chamber may be positioned against. The sample breath within the sensing chamber is desirably maintained within for prolonging contact against the sensor surface and also to prevent the sample breath from escaping into the rest of the housing by sealing the contact region with an interface such as a seal which encircles the sensing chamber. Preventing the breath sample from escaping into the rest of the housing not only may provide for better signal sensing and response speed but also avoids the contact against the other electronics contained within the housing.

However, due to the assembly tolerances of the flow control assembly, which may have a positional tolerance with respect to the sensor surface of up to, e.g., +/−0.010 in., the seal may be positioned upon a tapered surface which may be formed in an annular configuration around the sampling chamber. The tapered surface may be angled so that the tapered surface extends away from the contact region. When the seal is positioned upon the tapered surface, the seal is urged to push against the sensor surface with a spring constant in proportion to the angle of the tapered surface. This also allows for the seal to press against the sensor surface while providing sealing with a flatter force response than what a conventional compression gasket could provide by providing a relatively lower force across the geometric gap range especially if the sensor is pressure sensitive.

When a subject blows into the collection tube for submitting a breath sample, predicting a terminal value of the sensors in a limited-duration breath test may be difficult due to the stabilization time typically needed for many types of sensors to accurately detect parameters from the breath sample. For instance, gas sensors (such as CO sensors) may take up to 10-30 seconds of sampling time to stabilize and yield a final value. However, subjects may not be able to (or should not need to) exhale for more than 5-10 seconds into the collection tube in order to obtain an accurate reading. Hence, the final value may be estimated based upon the transient signals obtained from the sensor. The rate of stabilization may also be complicated due to various known or unknown variables such as current temperature or humidity levels at the time of sampling, previous dwell temperature or humidity levels, etc.

Hence, if the rates of stabilization are fixed or can be estimated accurately based on other known parameters, e.g. temperature, then the following process may be used in one variation. For instance, the sensor electronics in the unit may be calibrated using a gas of known concentration (e.g. 50 ppm CO) and the entire calibration curve may be recorded as a function of time, e.g., the sensor response may be recorded as a function of time. Alternatively, rather than the entire calibration curve, a sufficient portion of the calibration curve (and not just the terminal and plateau values) may be recorded and stored in memory.

During a test, the input response sensor curve may be associated with the calibration curve. The association may be accomplished using a number of different methods. In one variation, the sensor value at test time $t=t_1$ may be compared to the calibration value at $t=t_1$, where $t_1$ is a selected to be a time of interest, e.g., time at the peak, time at the end of the test, or a specific time during the test (e.g. 10 seconds, etc.). In another variation, a least-squares fit may be performed of the input sensor curve to the calibration curve multiplied by a constant, and optimizing for that constant. For example, a constant of 0.6 would mean the input value is calculated to be 0.6*the calibration value. The calibration constant is calculated for each device and may be based on the calibrated input from the subject. Finally, the final value may be determined by extrapolating the sample result based the calibrated curve.

If the rate of stabilization is not sufficiently well known for a sensor but the shape of the calibration curve is known, in particular an exponential settling function of the type $y(t)=y_{terminal}*(1-e^{-t/\tau})$, then the following process may be used. During a calibration test or a field test, any compensations may be performed (heuristical or theoretical) that allow the input curve to better fit a simple analytical function such as the exponential settling function. For example, the early part of the curve may be adjusted to compensate for diffusion speed to the sensor. Default values may be assumed for constants associated with the analytical function. In the case of the exponential settling function, a default value for tau, $\tau$, may be assumed. The goodness of fit of the (compensated) input data to the analytical function may be assessed and a determination may be made as to whether the good of fit is sufficient. Assuming goodness of fit is insufficient, an adjustment may be made of the value of the analytical function constants, $\tau$, based on the disparity between the input data and analytical function, e.g. overshoot or undershoot and steps may be repeated using an optimizing algorithm (e.g., binary search, executed on the constant tau) to evaluate for the best fit to the analytical function. Once the goodness of fit is sufficient, the optimized analytical function and input data may be used to predict the value of input analyte (CO), e.g., by estimating the terminal value. When performing calibration, this procedure may be used to set the sensitivity ($y_{terminal}/CO_{ppm}$) and when performing a test, this procedure may be used and the terminal value may be divided by the sensitivity to calculate the analyte level.

Over time, the sensors may begin to degrade with repeated use and the calibration data initially used may no longer be valid after some amount of time has passed. Thus, aging data may be used to determine typical behavior over time and also used to compensate the calibration data accordingly. For example, the approximate degradation of certain sensors may be known to be, e.g., 0.6% per month for the first six months and then 0.3% per month thereafter. With this known degradation rate, these parameters may be used to compensate the analysis of each measured value thereafter based upon the amount of time which has elapsed since the device was calibrated.

In another variation of the sampling unit, the device may additionally and/or alternatively incorporate one or more spirometers for monitoring or screening for various conditions, e.g., COPD, asthma, etc. The spirometer may be incorporated into the unit so that it is in fluid communication with a sample breath passing through the flow path to detect and/or monitor parameters. The spirometer may be wired to a processor within the unit or it may be wirelessly in communication with the personal electronic device or computer. Additionally, the flow path may include a flow switch to increase or decrease flow resistance along the flow path. When the subject breaths into the device, they may be instructed to exhale as vigorously as possible and the device may translate measured pressure into a flow rate to calculate, e.g., forced vital capacity (FVC) or forced expiratory volume, 1 second test (FEV1).

DETAILED DESCRIPTION OF THE INVENTION

In engaging individuals who smoke and quantifying their smoking behavior, methods and systems may be implemented to allow for improved measuring and quantifying of a smoker's behavior. Once the individual smoker is identified, the same methods and systems may allow for a learn and explore phase where the individual's specific smoking behavior can be tracked and quantified and the individual's behavioral data may also be tracked to identify potential triggers to smoking or simply to educate the individual on the extent of their smoking. These methods and systems also allow for a more active monitoring of the individual that has decided to engage in a quit program, where such monitoring allows the individual to self-monitor as well as monitoring by peers, coaches, or counselors.

Certain biometric data of the subject may be obtained by non-invasively detecting and quantifying the smoking behavior for a patient based on measuring one or more of the patient's biometric data such as CO level or exhaled CO level. However other biometric data can also be used. Such measurements or data collection can use a portable measuring unit or a fixed measuring unit, either of which communicates with one or more electronic devices for performing the quantification analysis. Alternatively, the analysis can be performed in the portable/fixed unit. For example, the portable unit can be coupled to a keychain, to the individual's cigarette lighter, cell phone, or other item that will be with the individual on a regular basis. Alternatively, the portable unit can be a stand-alone unit or can be worn by the individual.

Systems and methods for assisting a subject in quantifying and quitting their smoking behavior as well as details of how such a breath sensing device may be used or incorporated into such systems and methods are described in further detail in U.S. patent application Ser. No. 15/092,475 filed Apr. 6, 2016 (U.S. Pat. Pub. 2017/0055572) and U.S. patent application Ser. No. 15/258,921 filed Sep. 7, 2016 (U.S. Pat. Pub. 2017/0055573), each of which is incorporated herein by reference in its entirety and for any purpose.

Figure 1:
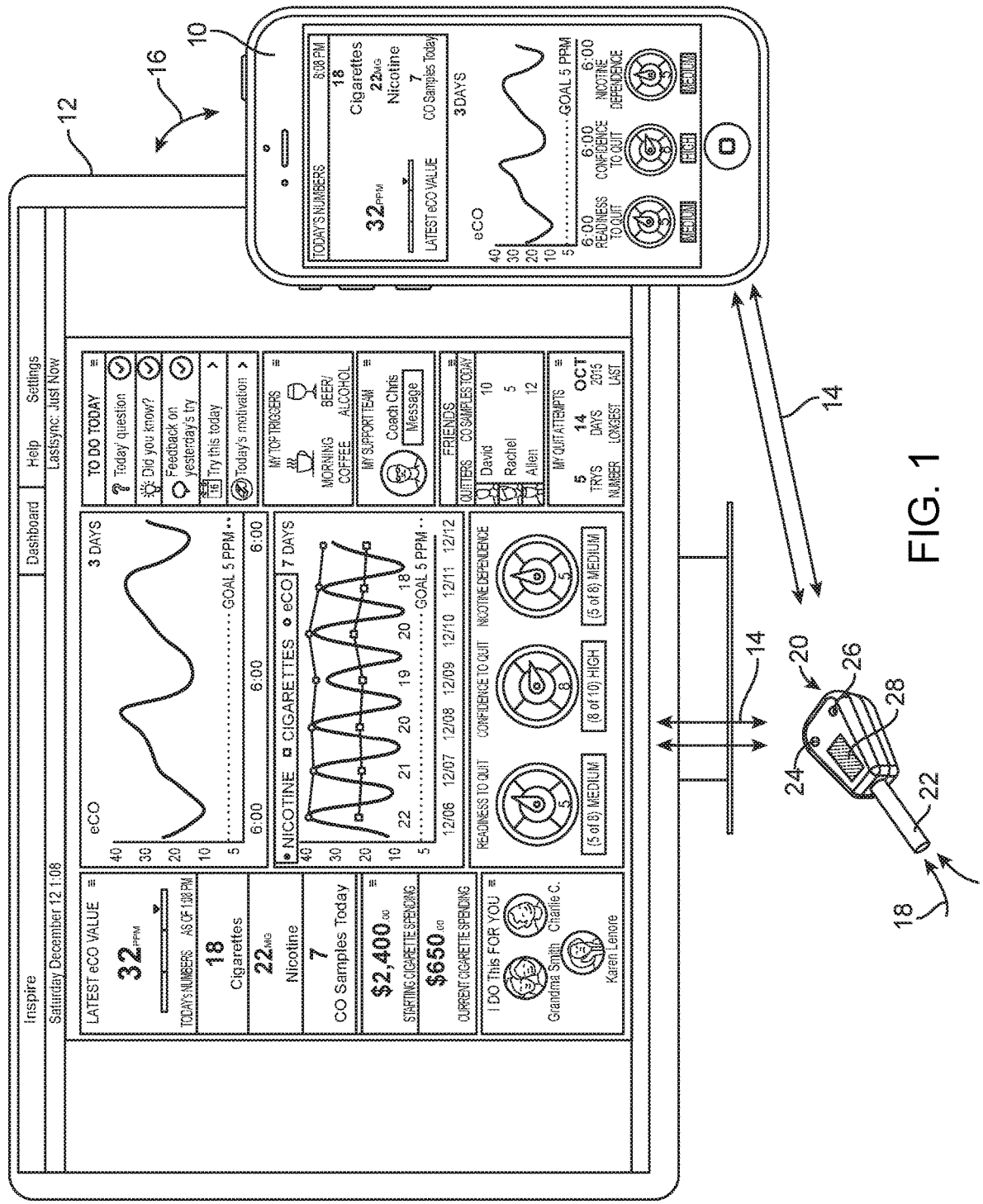
FIG. 1 illustrates a variation of a system which is able to receive the exhaled breath from a subject and detect various parameters and which can communicate with a one or more remote devices.

For instance, FIG. 1 illustrates one variation of a system and/or method in which a plurality of samples of biometric data are obtained from the individual and analyzed to quantify the individual's exposure to cigarette smoke such that the quantified information can be relayed to the individual, a medical caregiver, and/or other parties having a stake in the individual's health. The example discussed below employs a portable device 20 that obtains a plurality of samples of exhaled air from the individual with commonly available sensors that measure an amount of carbon monoxide within the sample of exhaled air (also referred to as exhaled carbon monoxide or eCO). However, the quantification and information transfer is not limited to exposure of smoking based on exhaled air. As noted above, there are many sampling mechanisms to obtain an individual's smoking exposure. The methods and devices described in the present example can be combined or supplemented with any number of different sampling mechanisms where possible while still remaining within the scope of the invention.

The measurement of exhaled CO level has been known to serve as an immediate, non-invasive method of assessing a smoking status of an individual. The levels of eCO levels for non-smokers can range between, e.g., 0 ppm to 6 ppm, or more particularly between, e.g., 3.61 ppm and 5.6 ppm.

As shown, a portable or personal sampling unit 20 may communicate with either a personal electronic device 10 or a computer 12. Where the personal electronic device 10 includes, but is not limited to a smart phone, cellular phone, or other personal transmitting device designed or programmed for receiving data from the personal sampling unit 20. Likewise, the computer 12 is intended to include a personal computer, local server, remote server, etc. Data transmission 14 from the personal sampling unit 20 can occur to both or either the personal electronic device 10 and/or the computer 12. Furthermore, synchronization 16 between the personal electronic device 10 and the computer 12 is optional. Either the personal electronic device 10, the computer 12, and/or the personal sampling unit 20 can transmit data to a remote server for data analysis as described herein. Alternatively, data analysis can occur, fully or partially, in a local device (such as the computer or personal electronic device). In any case, the personal electronic device 10 and/or computer 12 can provide information to the individual, caretaker, or other individual as shown in FIG. 1.

The personal sampling unit 20 receives a sample of exhaled air 18 from the individual via a collection tube 22. Hardware within the personal sampling unit 20 may include any commercially available electrochemical gas sensor that detects carbon monoxide (CO) gas within the breath sample, commercially available transmission hardware that transmits data 14 (e.g., via Bluetooth, cellular, or other radio waves to provide transmission of data). The transmitted data and associated measurements and quantification are then displayed on either (or both) a computer display 12 or a personal electronic device 10. Alternatively, or in combination, any of the information can be selectively displayed on the portable sampling unit 20.

The personal sampling unit 20 (or personal breathing unit) can also employ standard ports to allow direct-wired communication with the respective devices 10 and 12. In certain variations, the personal sampling unit 20 can also include memory storage, either detachable or built-in, such that the memory permits recording of data and separate transmission of data. Alternatively, the personal sampling unit can allow simultaneous storage and transmission of data. Additional variations of the device 20 do not require memory storage. In addition, the unit 20 can employ any number of GPS components, inertial sensors (to track movement), and/or other sensors that provide additional information regarding the patient's behavior.

The personal sampling unit 20 can also include any number of input trigger (such as a switch or sensors) 24, 26. As described below, the input trigger 24, 26 may allow the individual to prime the device 20 for delivery of a breath sample 18 or to record other information regarding the cigarette such as quantity of cigarette smoked, the intensity, etc. In addition, variations of the personal sampling unit 20 also associate a timestamp of any inputs to the device 20. For example, the personal sampling unit 20 can associate the time at which the sample is provided and provide the measured or inputted data along with the time of the measurement when transmitting data 14. Alternatively, the personal sampling device 20 can use alternate mechanisms to identify the time that the sample is obtained. For example, given a series of samples rather than recording a timestamp for each sample, the time periods between each of the samples in the series can be recorded. Therefore, identification of a timestamp of any one sample allows determination of the time stamp for each of the samples in the series.

In certain variations, the personal sampling unit 20 may be designed such that it has a minimal profile and can be easily carried by the individual with minimal effort. Therefore the input triggers 24 can comprise low profile tactile switches, optical switches, capacitive touch switches, or any commonly used switch or sensor. The portable sampling unit 20 can also provide feedback or information to the user using any number of commonly known techniques. For example, as shown, the portable sampling unit 20 can include a screen 28 that shows select information as discussed below. Alternatively or in addition, the feedback can be in the form of a vibrational element, an audible element, and a visual element (e.g., an illumination source of one or more colors). Any of the feedback components can be configured to provide an alarm to the individual, which can serve as a reminder to provide a sample and/or to provide feedback related to the measurement of smoking behavior. In addition, the feedback components can provide an alert to the individual on a repeating basis in an effort to remind the individual to provide periodic samples of exhaled air to extend the period of time for which the system captures biometric (such as eCO, CO levels, $H_2$ etc.) and other behavioral data (such as location either entered manually or via a GPS component coupled to the unit, number of cigarettes, or other triggers). In certain cases, the reminders can be triggered at higher frequency during the initial program or data capture. Once sufficient data is obtained, the reminder frequency can be reduced.

In obtaining the breath sample with the sampling unit 20, instructions may be provided on the personal electronic device 10 or computer display 12 for display to the subject in a guided breath test for training the subject to use the unit 20. Generally, the subject may be instructed, e.g., on the electronic device 10, to first inhale away from the unit 20 and then to exhale into the unit 20 for a set period of time. The unit 20 may optionally incorporate one or more pressure sensors fluidly coupled with, e.g., check valves, to detect if the subject inhales through the unit 20.

Figure 2:
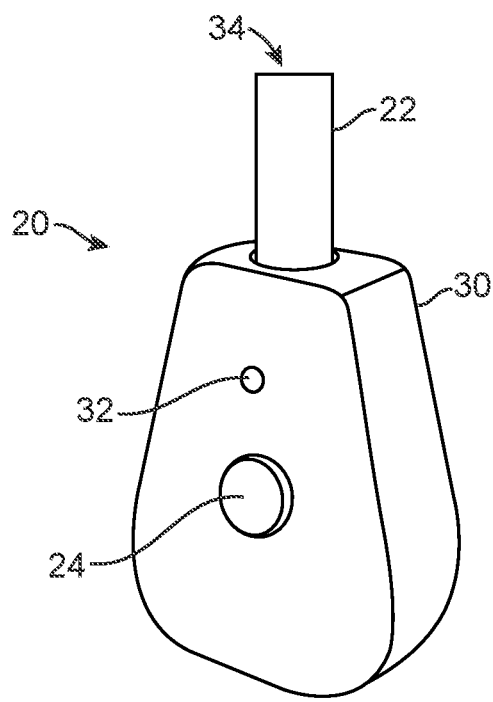
FIG. 2 illustrates a perspective view of one variation of a portable breath sensor.

Turning now to the personal sampling unit 20 itself, FIG. 2 illustrates a perspective view of one variation of the unit 20 which may generally comprise a housing 30 having a shape which allows for the user to hold and manipulate the unit 20 with a single hand. The housing may incorporate the input trigger 24 as well as one or more indicators such as indicator 32 which is shown as a light. The collection tube 22 may be comprised of a tube defining a lumen 34 and which extends from the housing 30.

Figure 3:
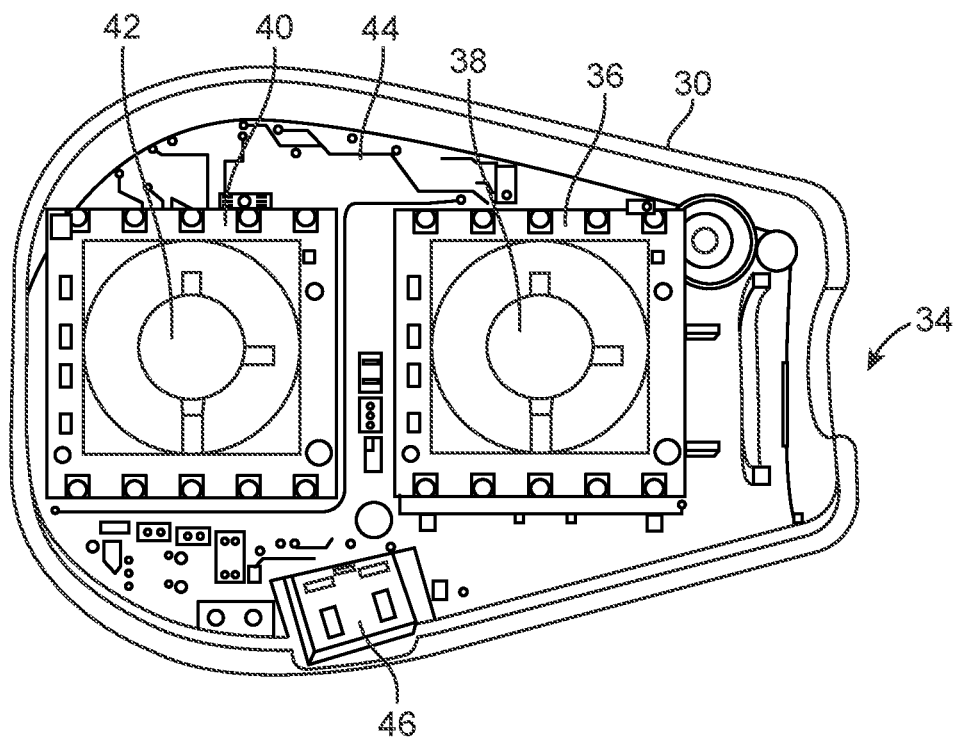
FIG. 3 illustrates one variation of the internal circuitry and sensors contained within the housing of the breath sensor.

FIG. 3 shows a portion of the housing 30 and collection tube 22 removed to show a top view of the sensors contained within. In this variation, a first sensor 38 and second sensor 42 (either or both of the sensors 38, 42 may include CO and $H_2$ sensors) are shown optionally positioned upon respect respective sensor platforms 36, 40 which in turn may be mounted upon a substrate such as a printed circuit board 44. Although in other variations, one or more sensors may be used depending upon the parameters being detected. In other variations, the one or more sensors may be mounted directly upon the printed circuit board 44. A power port and/or data access port 46 may also be seen integrated with the printed circuit board 44 and readily accessible by a remote device such as a computer, server, smartphone, or other device. As shown, multiple sensors 38, 42 or a single sensor may be used to detect the parameters from the sampled breath.

In other variations, at least one CO sensor or multiple CO sensors may be implemented alone. Alternatively, one or more CO sensors may be used along with one or more $H_2$ sensors in combination. If both a CO and $H_2$ sensor are used, the readings from the $H_2$ sensor may be used to account for or compensate for any $H_2$ signals detected by the CO sensor since many CO sensors have a cross-sensitivity to $H_2$ which is frequently present in sufficient quantity to potentially affect CO measurement in the breath of people. If a CO sensor is used without an $H_2$ sensor, various methods may be applied to reduce any $H_2$ measurement interference to a nominally acceptable level. However, the use of an $H_2$ sensor to directly measure and compensate for the presence of $H_2$ may facilitate CO measurement. The sensors may also include any number of different sensor types including chemical gas sensors, electrochemical gas sensors, etc. for detecting agents such as carbon monoxide in the case of detecting smoking related inhalation.

When detecting agents from breath samples from a subject, it is generally desirable to avoid temperature and humidity impacts on the sensors 38, 42 particularly in breath sensing devices which are compact as temperature swings and humidity may interfere with the detected signals in the sensors 38, 42. Larger breath sensing devices are able to readily contend with temperature and humidity variances due to their relatively larger mass and longer flow paths as the sampled breath temperature is reduced and moisture is removed prior to the breath sample reaching the sensor.

Figure 4A:
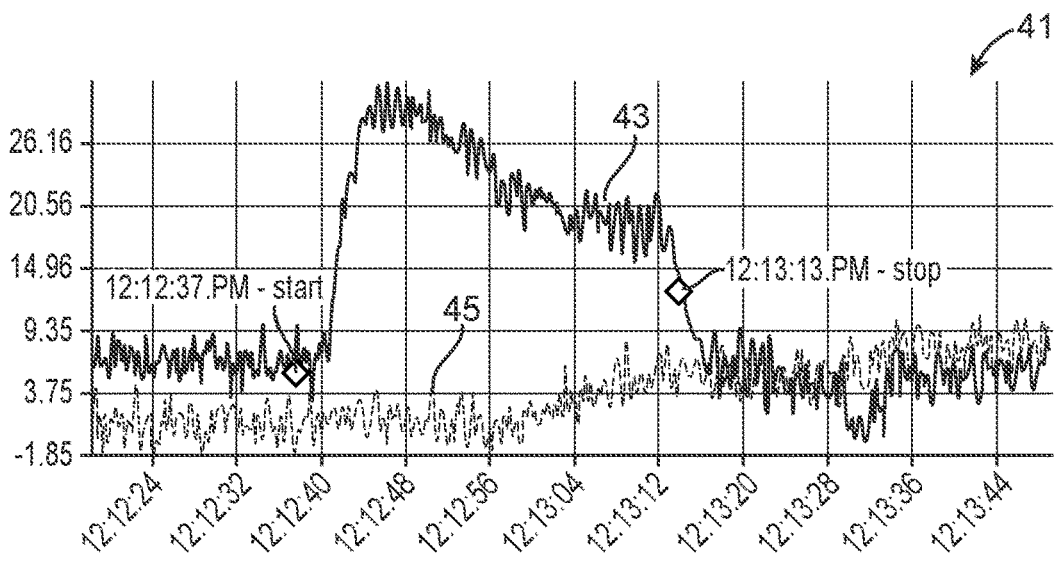
FIG. 4A illustrates a graph of a humid gas and the effects of humidity upon the readings.
Figure 4B:
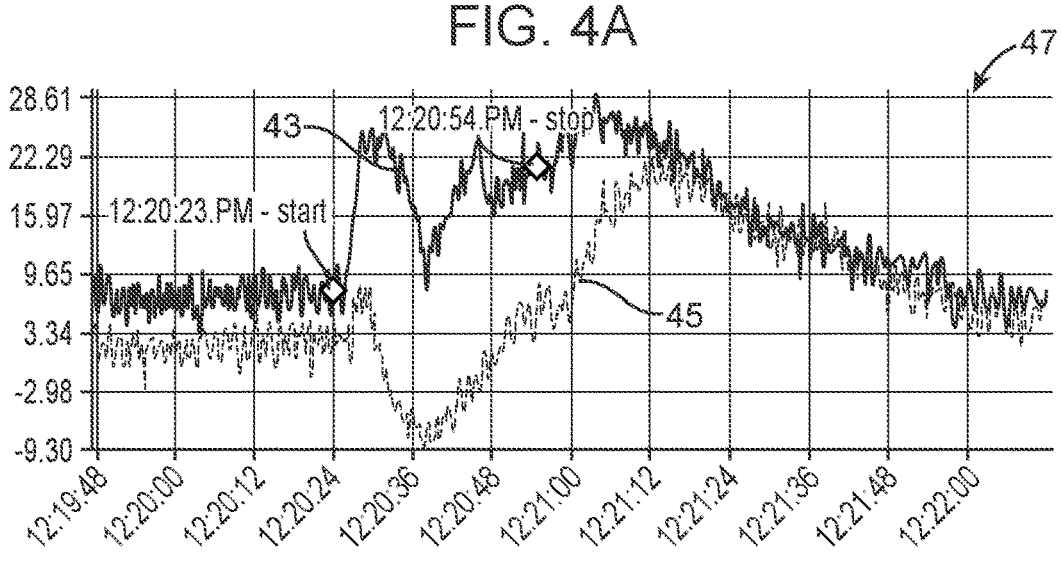
FIG. 4B illustrates a graph of a humid gas introduced at a relatively higher flow rate.
Figure 4C:
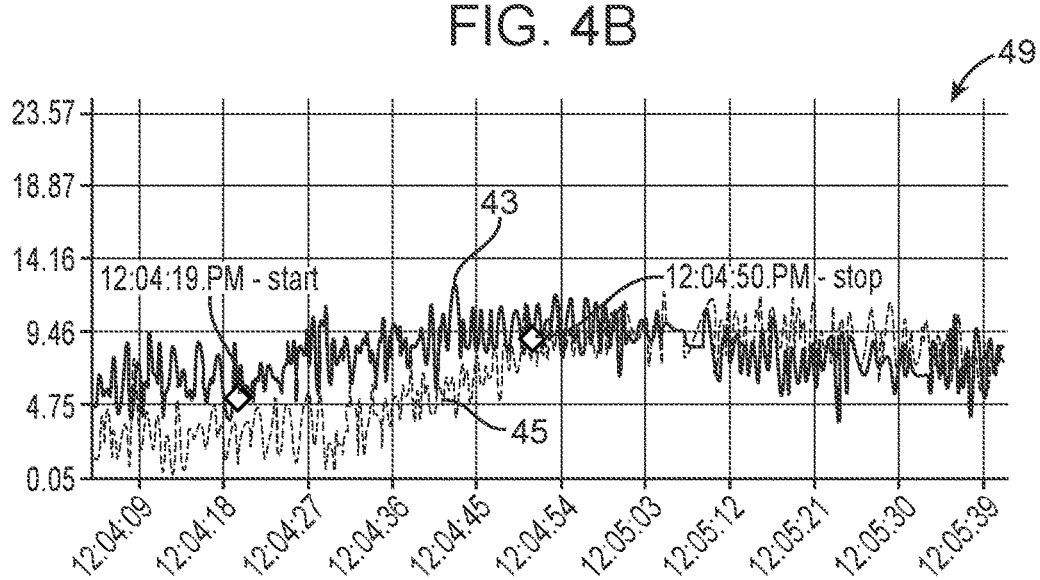
FIG. 4C illustrates a graph of a humid gas with diffusion pathways implemented.

As an example of the effects of humidity upon the sensors, FIGS. 4A to 4C illustrate how sensor readings may be affected if humidity is not mitigated. A humid gas with no gas analyte was passed over sensors and the CO level 43 and $H_2$ level 45 were measured at a medium flow rate and charted in graph 41, as shown in FIG. 4A. FIG. 4B illustrates graph 47 when the gas is introduced at a relatively higher flow rate. As shown, the CO level 43 and $H_2$ level 45 result in more chaotic effects due not only to the humidity but also from the flow dynamics. The graphs 41, 47 demonstrate some of the difficulties in compensating for humidity as well as the flow dynamics. While differential temperature of the breath and device can affect the sensor readings, condensation can also create large signal differentials as variability due to moisture effects may be relative high in sample-to-sample readings if the moisture effects are not mitigated. In contrast, FIG. 4C shows graph 49 of the CO level 43 and $H_2$ level 45 measurements at a medium flow rate with diffusion pathways implemented, as described herein.

Hence, the diffusion pathways that the sampled breath follows to the sensors 38, 42 helps to minimize the equivalent signal from breath humidity. Additionally, the implementation of algorithmic extrapolation of relatively short breaths still enable accurate approximation of true values, as described in further detail herein. While creating diffusion resistance may reduce the effects of humidity, diffusion resistance may also increase the sensor equilibration time which may make extrapolation relatively more difficult, e.g., by increasing the time required to achieve a certain level of accuracy. However, within the context of a relatively small sampling unit 20, the implementation of these mechanisms or processes enable the detection and processing of optimal signals.

Figure 5A:
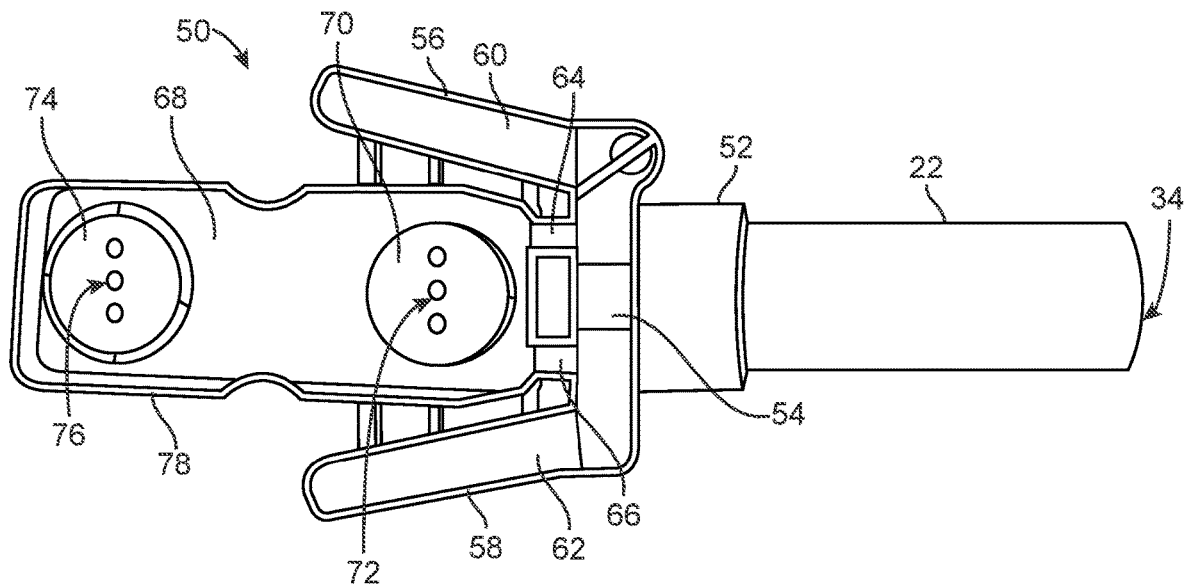
FIG. 5A illustrates a top view of one variation of a flow path control device.
Figure 5B:
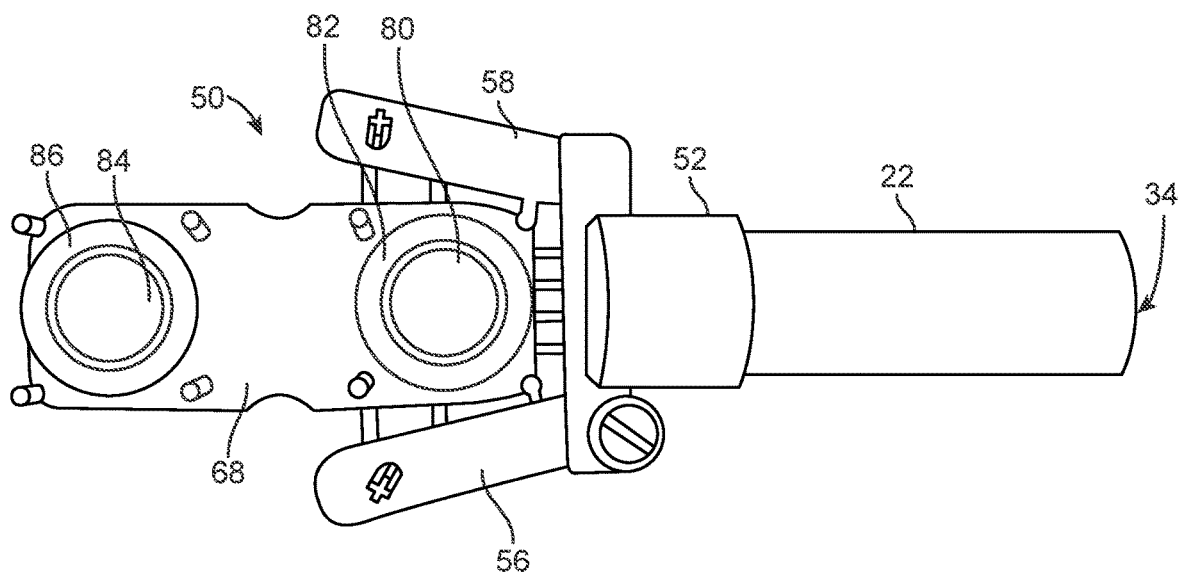
FIG. 5B illustrates a bottom view of the flow path control device of FIG. 4A.

In order for a relatively smaller device such as the personal sampling unit 20 described herein to accurately detect breath samples, one or several mechanisms may be employed to filter out moisture from the breath sample as well as reduce its temperature. FIGS. 5A and 5B illustrate respective top and bottom views of a flow control assembly 50 which may be incorporated into the housing 30 for controlling the flow of a breath sample to the sensors 38, 42. The assembly 50 may have a proximal receiving channel 52 into which the collection tube 22 may be inserted and retained. The lumen 34 of the collection tube 22 may be fluidly connected through the proximal receiving channel 52 and into a dispersion channel 54 which extends into and is fluidly coupled to one or more secondary channels 56, 58 which define corresponding second fluid pathways 60, 62 extending away from the dispersion channel 54, e.g., at an angle relative to the dispersion channel 54. While two secondary channels 56, 58 are shown extending opposite to one another away from the dispersion channel 54, other variations may incorporate a single channel or more than two channels.

One or more primary channels 64, 66 may further extend away from and fluid coupled with the dispersion channel 54 so that the primary channels 64, 66 open into a main receiving channel 68 which is defined by a barrier 78 formed around the receiving channel 68. The illustration shows two primary channels 64, 66 in parallel which divide the flow into at least two different paths; however, a single primary channel or more than two primary channels may be used in other variations. Regardless, the receiving channel 68 may be in fluid communication with the first and second sensors 38, 42 through openings 72, 76 extending into respective first and second sampling chambers 70, 74 which are formed as individual chambers for receiving the sample breath directly over the sensors 38, 42.

The dispersion channel 54 helps to divert a majority of the sampled breath into the secondary channels 56, 58 so that a relatively smaller portion of the breath passes through the primary channels 64, 66 and into the receiving channel 68. For instance, about 80% of the breath sample may be diverted into the secondary channels 56, 58 where it may then be vented out from of the housing 30. The remaining, e.g., 20% of the breath sample, may then enter into the receiving channel 68 so that the diverted flow helps to decrease the moisture level in the sampled breath. Additionally, the relatively larger volume defined by the receiving channel 68 may further help to reduce the temperature of the sampled breath.

The openings 72, 76 extending into the respective first and second sampling chambers 70, 74 are sized to be relatively smaller and may number from a single opening to multiple openings which help to further maintain the flow rate of the sampled breath entering the sampling chambers 70, 74 to a minimum flow rate of, e.g., about 4 mL/sec.

Contained within the first and second sampling chambers 70, 74 are respective first and second filters 80, 84 which further help to remove any additional moisture from the sampled breath. Additionally, respective first and second seals 82, 86 may surround the sampling chambers 70, 74 to contain the sampled breath over the sensors for detection. These first and second filters 80, 84 help to diffuse the flow path through a matrix, e.g., porous material, which not only removes moisture but also helps to further reduce the temperature of the sampled breath due to their additional thermal mass. The filters 80, 84 may be comprised of various materials that also filter out various chemicals such as alcohols, sulfur compounds, carbon monoxide, etc.

Figure 6:
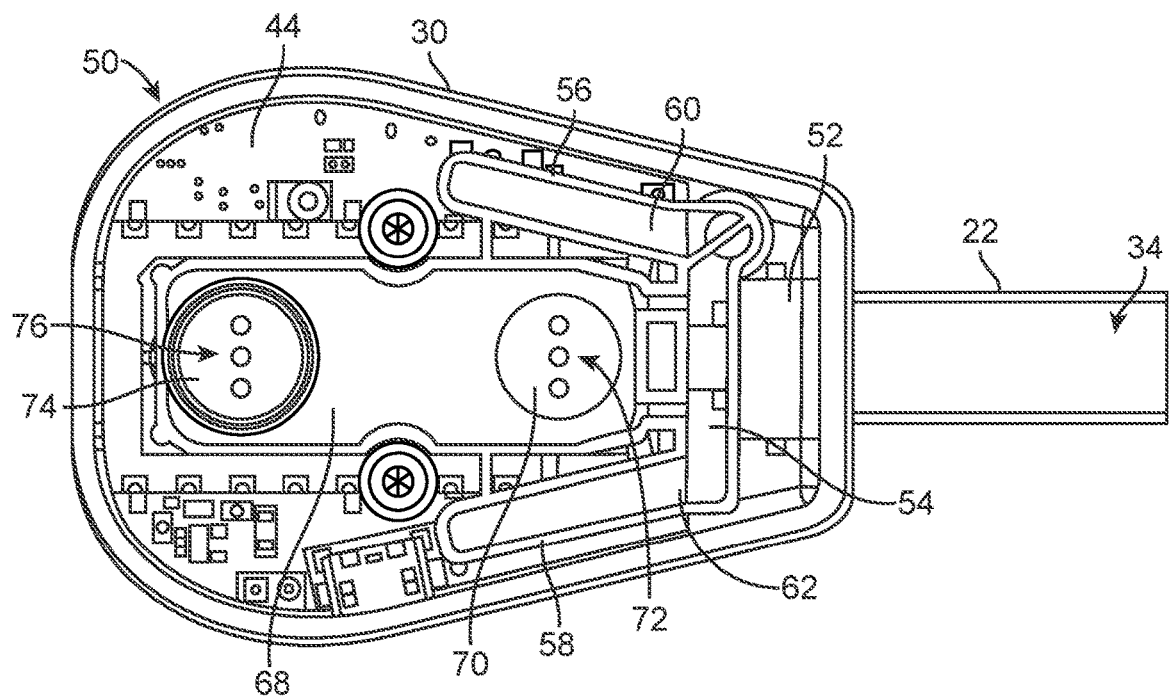
FIG. 6 illustrates a top view of the flow path control device positioned over the sensors.
Figure 7:
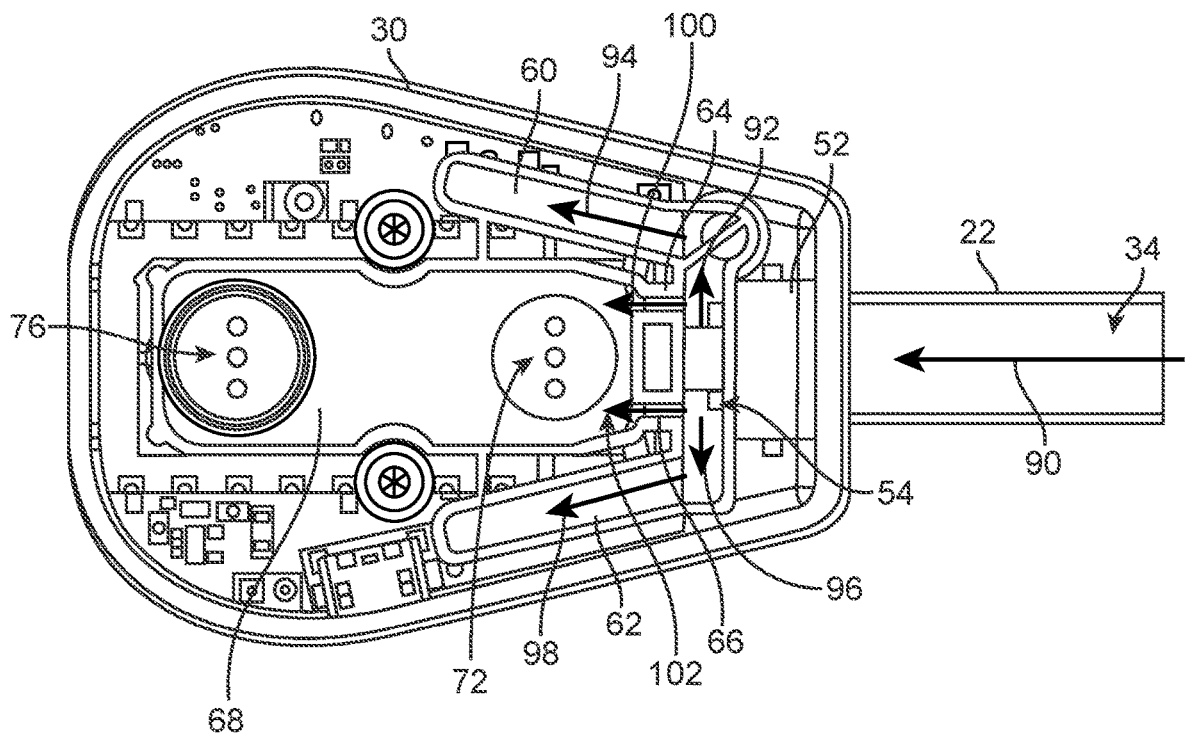
FIG. 7 illustrates a top view of the flow path control device with the various flow paths shown.

FIG. 6 shows a top view of the flow control assembly 50 incorporated into the housing 30 and sealed into positioned over the sensors 38, 42 such that the sampled air entering through the lumen 34 is contained within the assembly 50. As illustrated, the first and second sampling chambers 70, 74 are positioned over their respective first and second sensors 38, 42. FIG. 7 illustrates an example of the flow path that a sampled breath may follow. The initial breath 90 is shown entering the lumen 34 when exhaled by the subject. The breath enters the dispersion chamber 54 where a majority of the sample 92, 96, e.g., about 80%, is diverted through the chamber 54 and into respective second fluid pathways 60, 62 defined by secondary channels 56, 58. The remaining sample 100, 102, about 20%, enters through the primary channels 64, 66 and into the receiving channel 68 where the breath may then enter through the openings 72, 76 and into contact with the sensors 38, 42. In other variations, more than 50% of the breath sample may be diverted so that less than 50% of the breath sample enters into the receiving channel.

Figure 8:
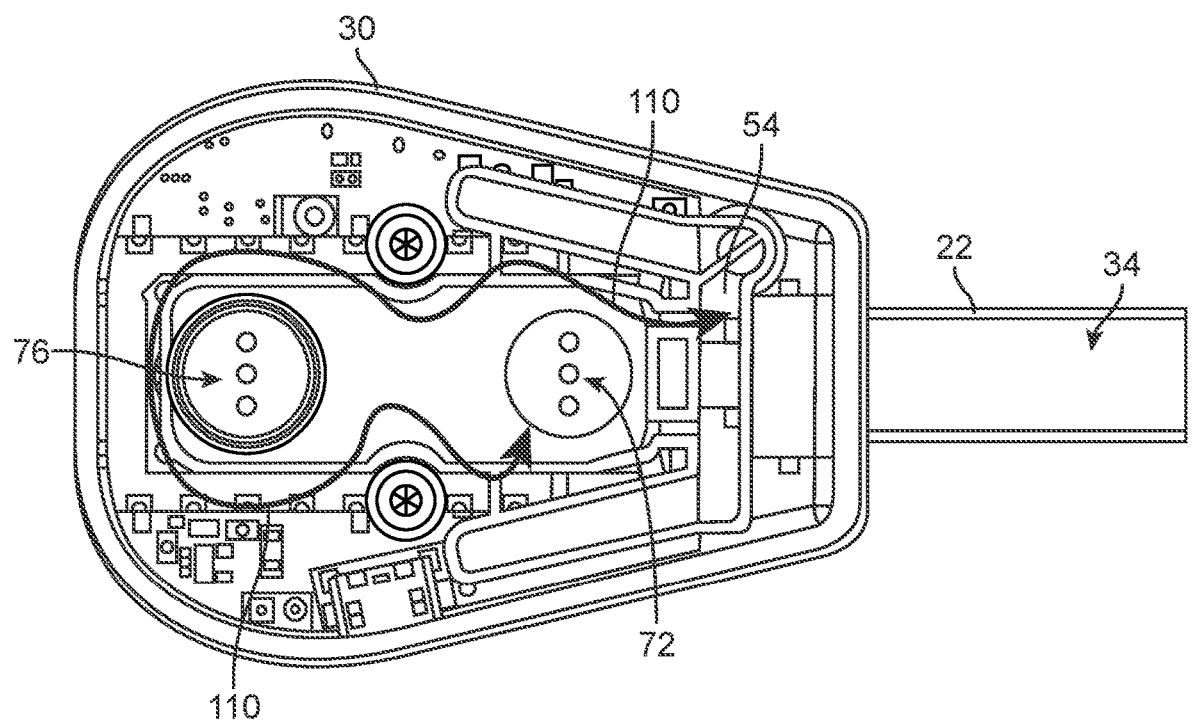
FIG. 8 illustrates a top view of another variation of a flow path control device showing how the flow path may be configured to be tortuous through the breath sensor.
Figure 9:
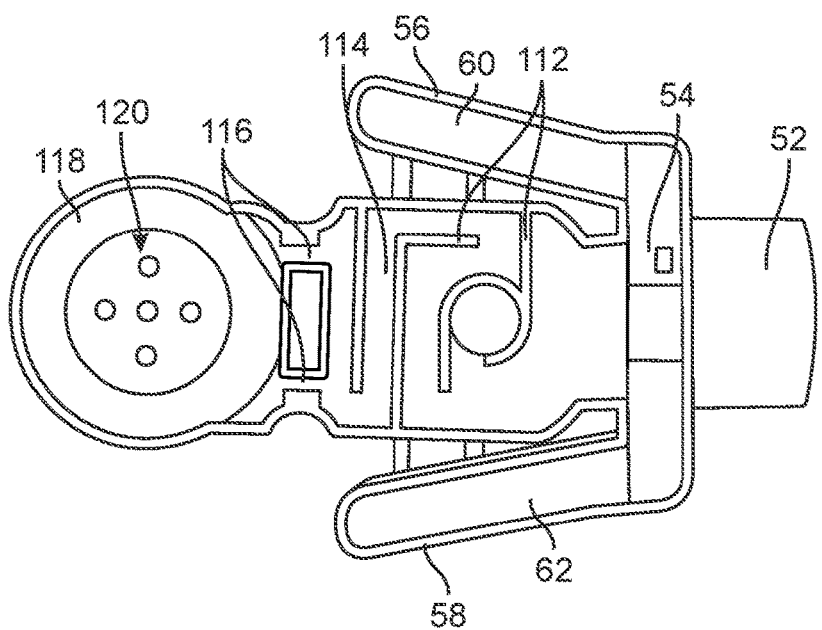
FIG. 9 illustrates a top view of another variation of a flow path control device showing another configuration of a tortuous flow path.

Another variation for reducing moisture and cooling the sampled breath may include incorporating a tortuous flow path which increases the surface area in contact with the sampled breath. This may include a coiled path or a maze which helps to drop the temperature and further allows for moisture to condense out of the breath and onto the surface area. FIG. 8 shows an example of how the breath sample passing from the dispersion chamber 54 may be forced into an exemplary tortuous flow path such as a circuitous loop 110 within the housing 30. The variation shown is intended to be illustrative and any number of tortuous flow paths may be configured. FIG. 9 shows another variation where the flow path is configured into a maze pattern. The sampled breath may leave the dispersion chamber 54 and encounter one or more barriers or baffles 112 which form the tortuous flow path 114. The sampled breath may pass through one or more channels 116 and enter a chamber 118 for entry through one or more openings 120 for sampling, as described herein.

Figure 10A:
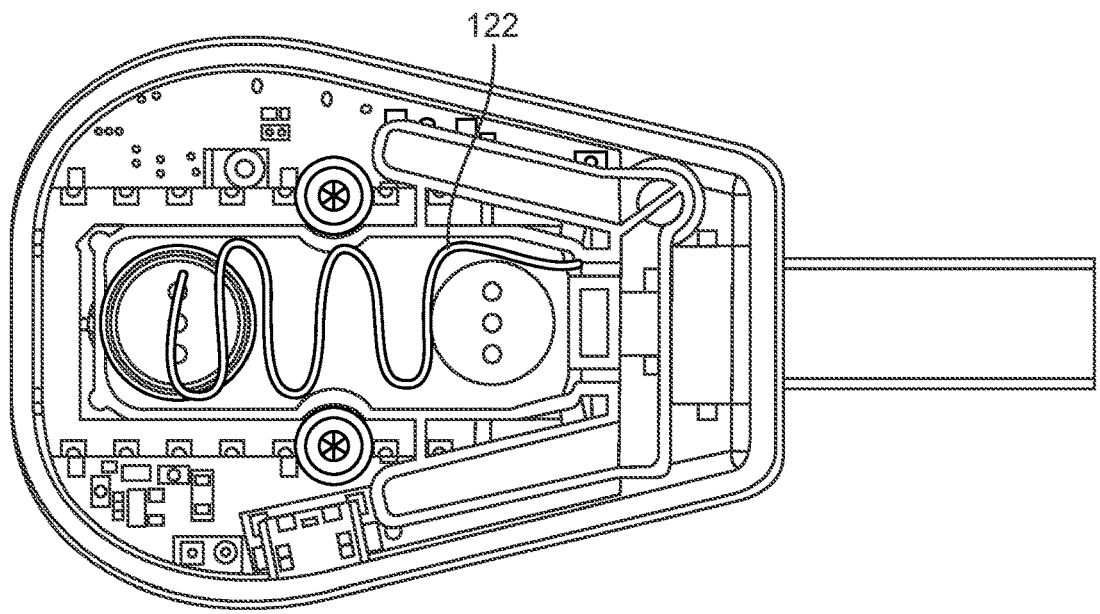
FIG. 10A illustrates a top view of another variation of a flow path control device which may utilize tubing coiled in any number of configurations.
Figure 10B:
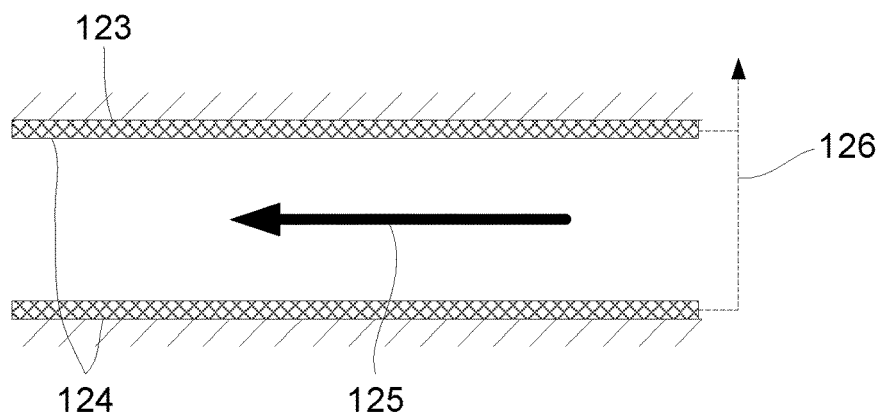
FIG. 10B illustrates an exemplary side view of a variation of a flow path incorporating a moisture-permeable membrane.

In yet another variation, rather than utilizing barriers or baffles to create a tortuous flow path, tubing 122 may be used for flowing the breath sample. The tubing 122, as illustrated in FIG. 10A, may be coiled in any number of configurations and the tubing itself may be fabricated from a material such as a synthetic polymer, e.g., sulfonated tetrafluoroethylene based fluoropolymer-copolymer such as Nafion, which may facilitate moisture removal. Alternatively, moisture may be removed from the sample by utilizing, e.g., a moisture-permeable membrane 124 along the flow path 123 or a hygroscopic material such as silica that may absorb the moisture from the sample 125, as shown in FIG. 10B. In these variations where moisture is condensed or absorbed along the flow path, the condensed water is desirably removed 126 from the flow assembly. Removal may be accomplished in one variation by increasing a number of vent holes (e.g., vent holes 130 as shown below in FIG. 11A) from the flow path to the environment while in another variation, a water transport membrane, e.g., Nafion or another water-permeable solid, may be used to transport the water away from the flow assembly.

Figure 10C:
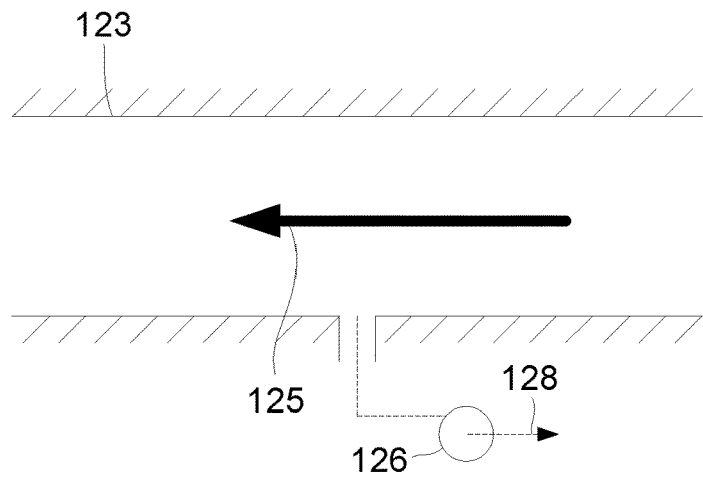
FIG. 10C illustrates an exemplary side view of another variation of a flow path incorporating an active pumping mechanism.

In yet another variation, an active mechanism such as a pump 126 may be used to draw a portion 128 of the sample 125 from the flow path 123 after the initial puff from the subject is introduced into the unit. FIG. 10C shows an example of how the portion 128 of exhaled breath may be drawn from the sample 125 by actuating the pump 126 after the breath is initially introduced through the flow path 123. This process may help to reduce the amount of moisture in the portion 128 before it is measured by the sensor.

Figure 11A:
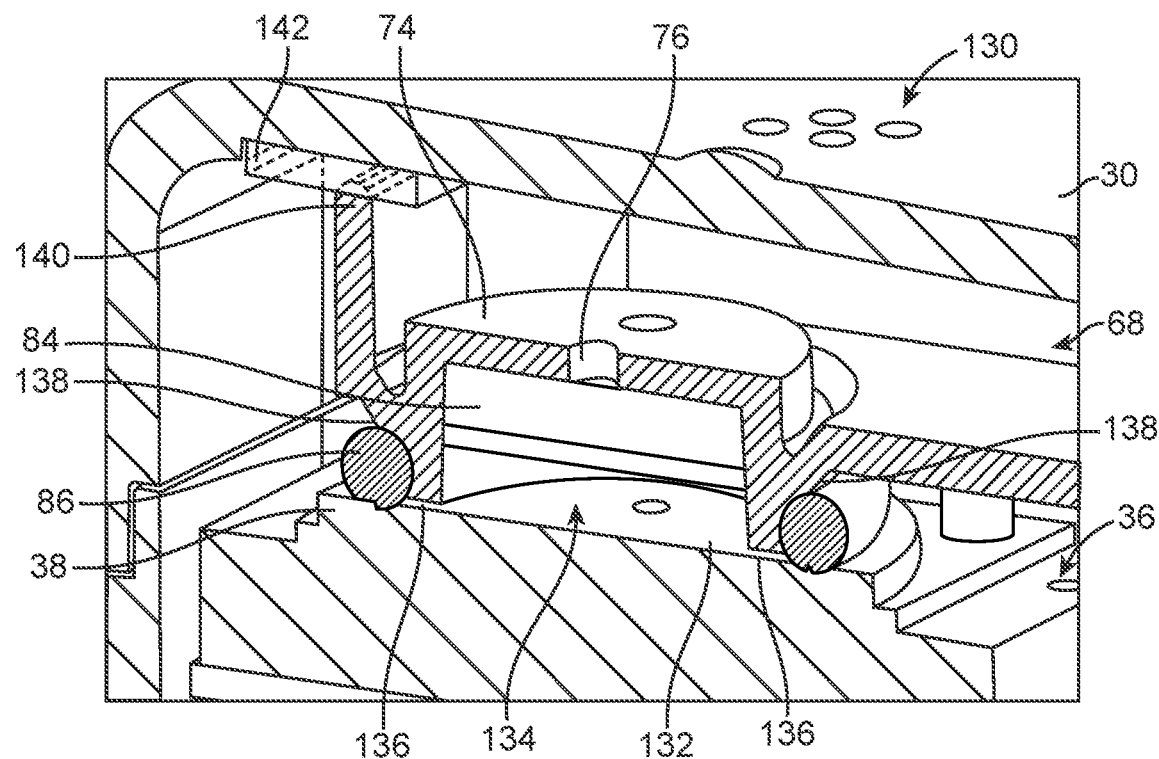
FIG. 11A illustrates a cross-sectional perspective view of a sensor enclosed by a seal which is urged into contact via a tapered interface.

Once the breath sample has been introduced through the openings 76 and past the filter 84, the sample may come be introduced within a sensing chamber 134 contained within an interior of the sampling chamber 74 where it comes into contact with the sensor 38, as illustrated in the cross-sectional detail perspective view of FIG. 11A. The gas diffusion into the sampling chambers may depend in part upon the size and number of openings into the sensing chambers and the presence of the one or more filters 84 may function as a capacitor for humidity. Hence, the sample breath passing over the sampling chambers may be diffused at a relatively slower rate into the sensing chamber 134 and into contact against the sensor 38. Despite the sample breath passing over the one or more openings 76, the net flow of the sample breath passing into the sampling chamber 74 is zero as the chamber 74 remains a sealed environment aside from the openings 76. The sample breath that does arrive within the sensing chamber 134 and into contact with the sensor 38 does so by via diffusion through the openings 76 and the one or more filters 84.

The surface 132 of the sensor 38 generally presents a planar face against which a contact region 136 of the sampling chamber 74 may be positioned against. The sample breath within the sensing chamber 134 is desirably maintained within for contacting against the sensor surface 132 and also to prevent the sample breath from escaping into the rest of the housing 30 by sealing the contact region 136 with an interface such as a seal 86 which encircles the sensing chamber 134. Preventing the breath sample from escaping into the rest of the housing 30 not only may provide for better signal sensing and response speed but also avoids the contact against the other electronics contained within the housing. The sample breath is prevented from escaping from the receiving channel 68 by the barrier 140 which may be sealed against the housing interior by a seal 142.

It is still desirable to divert or vent a majority of the sample breath flow as a greater flow over the diffusion chambers may increase net moisture content and hence increase the dew point, $T_d$, whereas a reduction of the dew point may increase the sensor response.

Figure 11B:
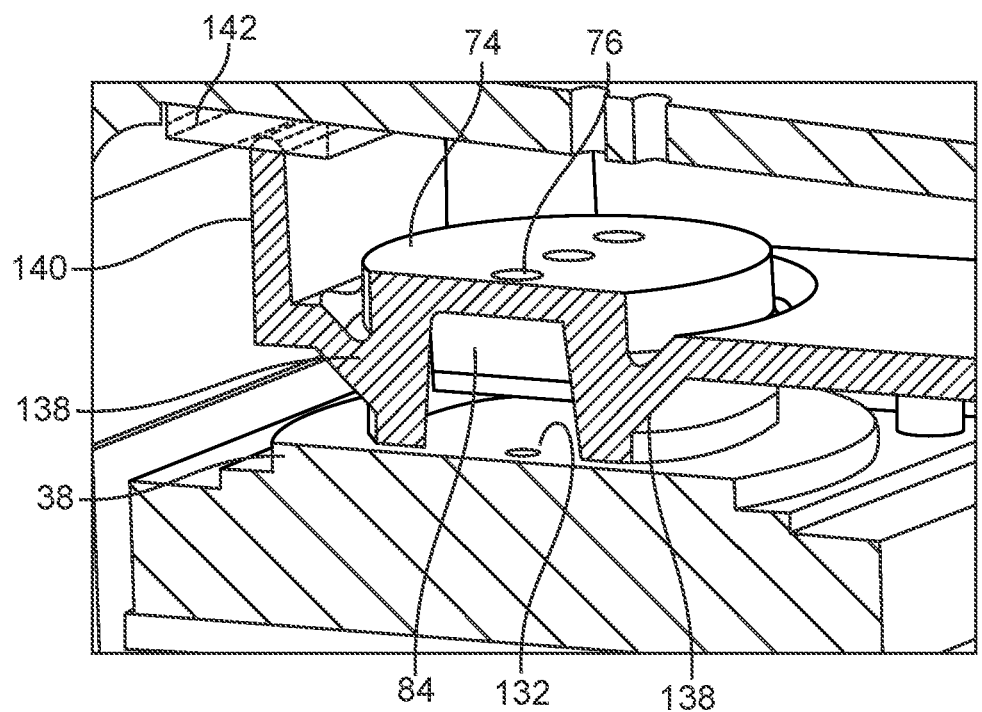
FIG. 11B illustrates the tapered interface of FIG. 11A with the seal removed for clarity.
Figure 11C:
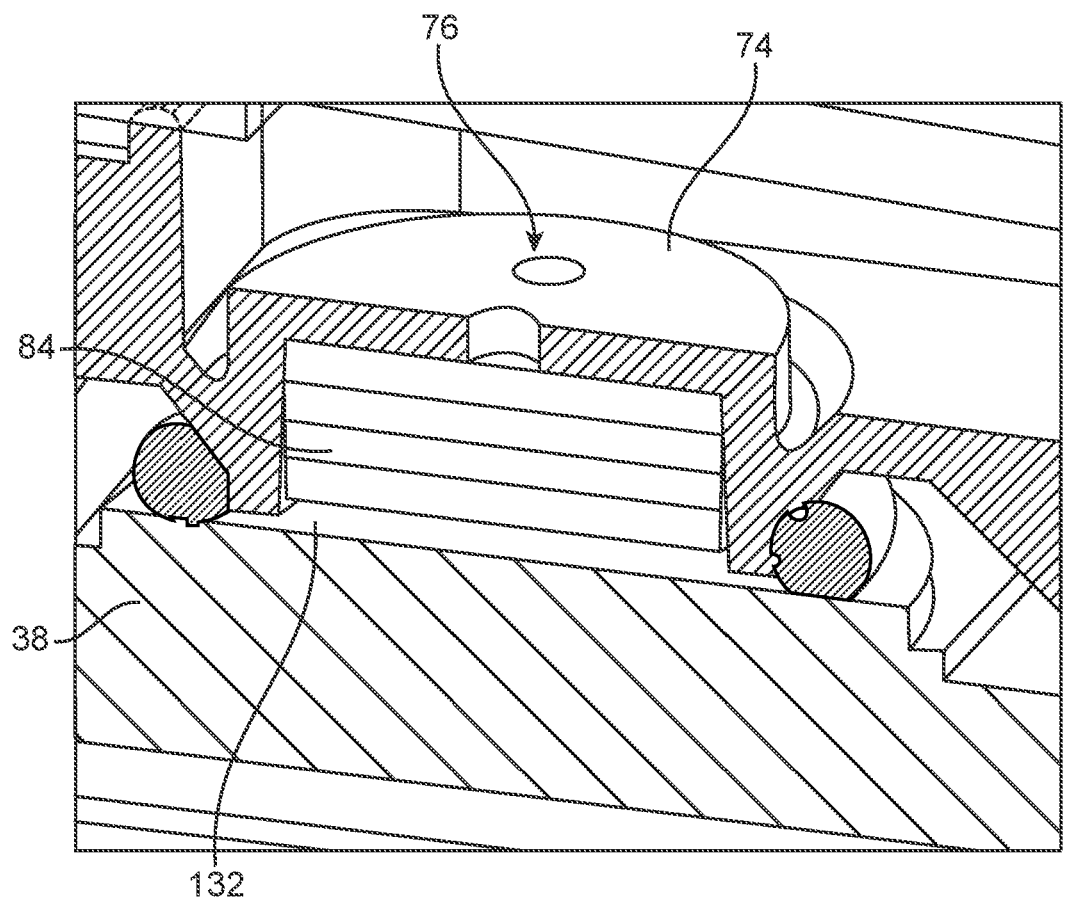
FIG. 11C illustrates a cross-sectional detail perspective view of another variation of a sampling chamber.

Due to the assembly tolerances of the flow control assembly 50, which may have a positional tolerance with respect to the sensor surface 132 of up to, e.g., +/−0.010 in., the seal 86 may be positioned upon a tapered surface 138 which may be formed in an annular configuration around the sampling chamber 74. The tapered surface 138 may be angled so that the tapered surface 138 extends away from the contact region 136 as shown in FIG. 11B which illustrates the interface of FIG. 11A with the seal 86 removed for clarity purposes only. When the seal 86 is positioned upon the tapered surface 138, the seal 86 is urged to push against the sensor surface 132 with a spring constant in proportion to the angle of the tapered surface 138. This also allows for the seal 86 to press against the sensor surface 132 while providing sealing with a flatter force response than what a conventional compression gasket could provide by providing a relatively lower force across the geometric gap range especially if the sensor 38 is pressure sensitive. Furthermore, the use of the seal 86 upon the tapered surface 138 helps to accommodate displacement due to tolerances of the contact region 136 and/or flow control assembly 50 for up to half the cross-sectional diameter of the seal 86, e.g., 0.070 in. FIG. 11C illustrates a cross-sectional detail perspective view of another variation of a sampling chamber 74 having multiple (e.g., four or more) filter layers contained within for filtering out the sampled breath.

With respect to the sampling chambers, its volume for receiving the sampled breath through the openings 76 may vary. In one variation, the volume may be, e.g., approximately 0.13 mL with 3×1.2 mm diameter openings 76 (3.4 mm²). A larger or smaller sampling chamber may be used and the area or size of the openings may change linearly with chamber volume. Thus, a ratio of opening area per chamber volume may be used as an indicator for determining optimal opening size and sampling chamber volume. This ratio of, e.g., about 25 mm²/mL, works well for CO and the ratio may change with the target gas as a smaller ratio may be more effective in blocking water. For instance, $H_2$ diffuses relatively faster than CO and so a ratio of about 10 mm²/mL would be effective if $H_2$ were the main gas of interest.

The sampling chamber may be filled with a porous or fibrous material that functions as a filter that can absorb moisture. This will not only remove some moisture from the gas diffusing through, but will also preferentially slow down the diffusion of moisture that does ultimately diffuses to the sensor. Furthermore, the filter material may be selected so that it removes unwanted contaminants, such as volatile organic compounds (VOCs). Materials such as activated carbon may be selected as it removes moisture and also many contaminants including alcohol which is particularly applicable for breath sensing.

Additionally, the ideal diffusion chamber geometry may also depend on the sensor. For instance, a relatively fast sensor may be able to handle a "slower" diffusion chamber characteristic, but a sensor with faster detection characteristics may be limited by the type and construction of the sensor.

When a subject blows into the collection tube 22 for submitting a breath sample, predicting a terminal value of the sensors 38, 42 in a limited-duration breath test may be difficult due to the stabilization time typically needed for many types of sensors to accurately detect parameters from the breath sample. For instance, gas sensors (such as CO sensors) may take up to 10-30 seconds of sampling time to stabilize and yield a final value. However, subjects may not be able to (or should not need to) exhale for more than 5-10 seconds into the collection tube 22 in order to obtain an accurate reading. Hence, the final value may be estimated based upon the transient signals obtained from the sensor.

During a test 156, the input response sensor curve may be associated with the calibration curve. The association may be accomplished using a number of different methods. In one variation, the sensor value at test time $t=t_1$ may be compared to the calibration value at $t=t_1$, where $t_1$ is a selected to be a time of interest, e.g., time at the peak, time at the end of the test, or a specific time during the test (e.g. 10 seconds, etc.). In another variation, a least-squares fit may be performed of the input sensor curve to the calibration curve multiplied by a constant, and optimizing for that constant. For example, a constant of 0.6 would mean the input value is calculated to be 0.6*the calibration value. The calibration constant is calculated for each device and may be based on the calibrated input from the subject. Finally, the final value may be determined 158 by extrapolating the sample result based the calibrated curve.

Figure 12:
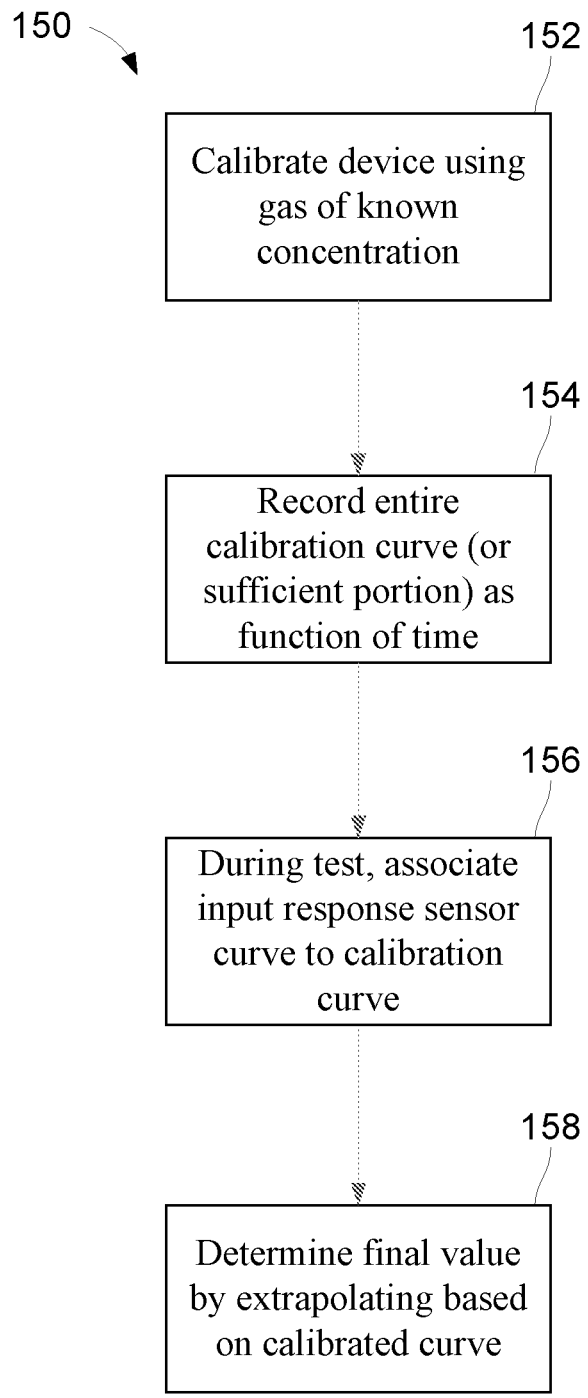
FIG. 12 illustrates a diagram of one method for estimating a final value of a sensor based on calibrated information.

Hence, if the rates of stabilization are fixed or can be estimated accurately based on other known parameters, e.g. temperature, then the process illustrated in the diagram 150 of FIG. 12 may be used in one variation. For instance, the sensor electronics in the unit 20 may be calibrated 152 using a gas of known concentration (e.g. 50 ppm CO) and the entire calibration curve may be recorded 154 as a function of time, e.g., the sensor response may be recorded as a function of time. Alternatively, rather than the entire calibration curve, a sufficient portion of the calibration curve (and not just the terminal and plateau values) may be recorded and stored in memory. The rate of stabilization may also be complicated due to various known or unknown variables such as current temperature or humidity levels at the time of sampling, previous dwell temperature or humidity levels, etc.

Figure 13A:
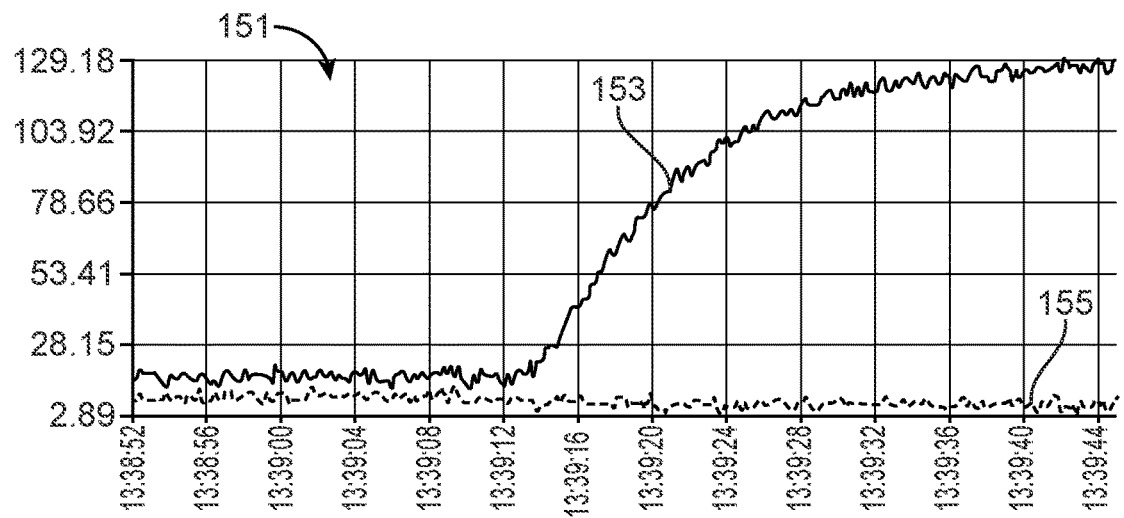
FIG. 13A illustrates a graph of a calibration curve of a gas having a known CO concentration.
Figure 13B:
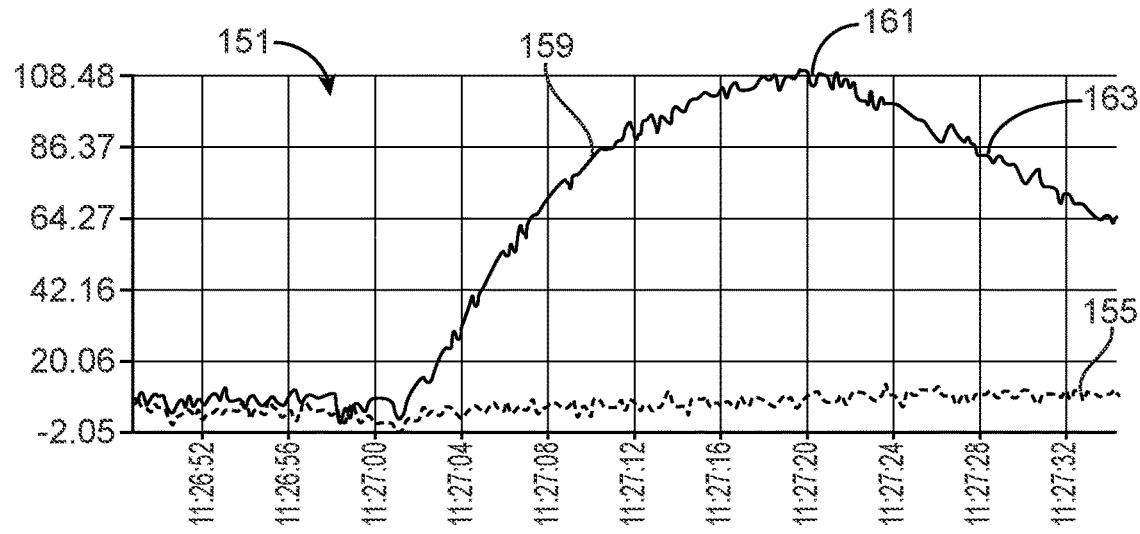
FIG. 13B illustrates a graph of a test sample obtained where the sample time is less than the calibration curve.
Figure 13C:
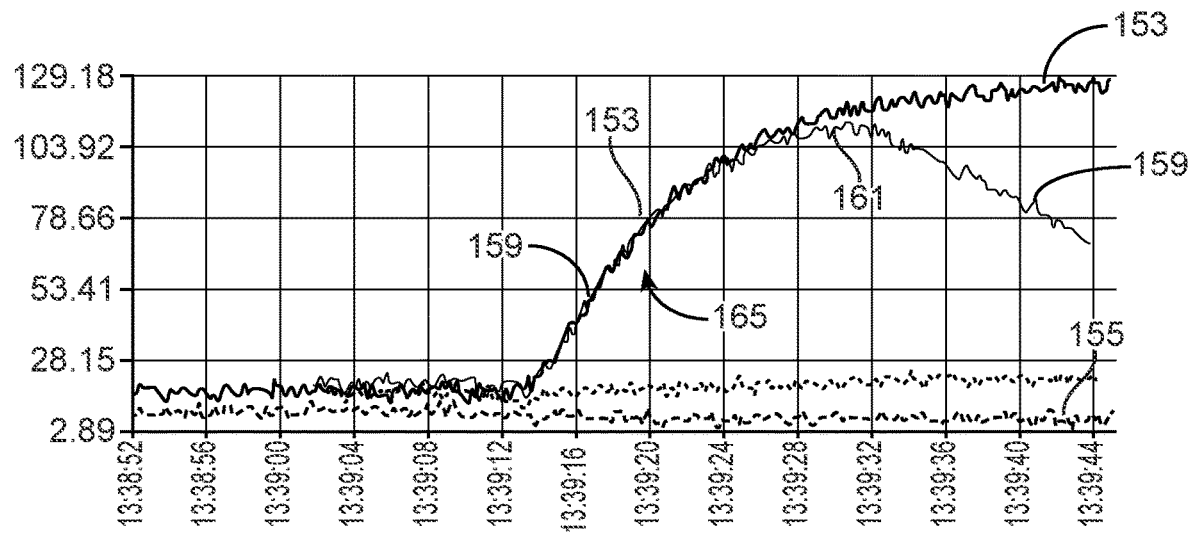
FIG. 13C illustrates an association between the known calibration curve and the obtained test sample for determining a final output value.

FIG. 13A illustrates an example of a graph 151 showing a calibration curve 153 of a gas having a known CO concentration and a curve 155 of a known $H_2$ concentration as described above in steps 152 and 154. The calibration curve may be obtained with a sample of, e.g., 50 ppm CO, measured over a period of, e.g., about 30 sec. This calibration curve may be used as a baseline where 129 mV=50 ppm is derived. FIG. 13B shows the graph 157 with a sample curve 159 of a test sample where 50 ppm CO for approximately 15 sec. Because the obtained test result is less than the length of the calibration curve 153 (e.g., if the subject is unable to continue blowing the sample breath), the detected signal may register a peak value 161 relatively early and begin to show a decrease 163. With the known calibrated curve 153, the sample curve 159 may be compared and associated with the calibrated curve 153, as described in step 156 and as shown in FIG. 13C. The sample curve 159 when compared against the calibrated curve 153 illustrates how the peak value 161 (for 50 ppm) is unable to reach the full sensor signal value in the recorded time of 15 seconds yet the algorithm may fit the data 165 to the exponential function, described herein, and determine that the final value as described in step 158.

Figure 14:
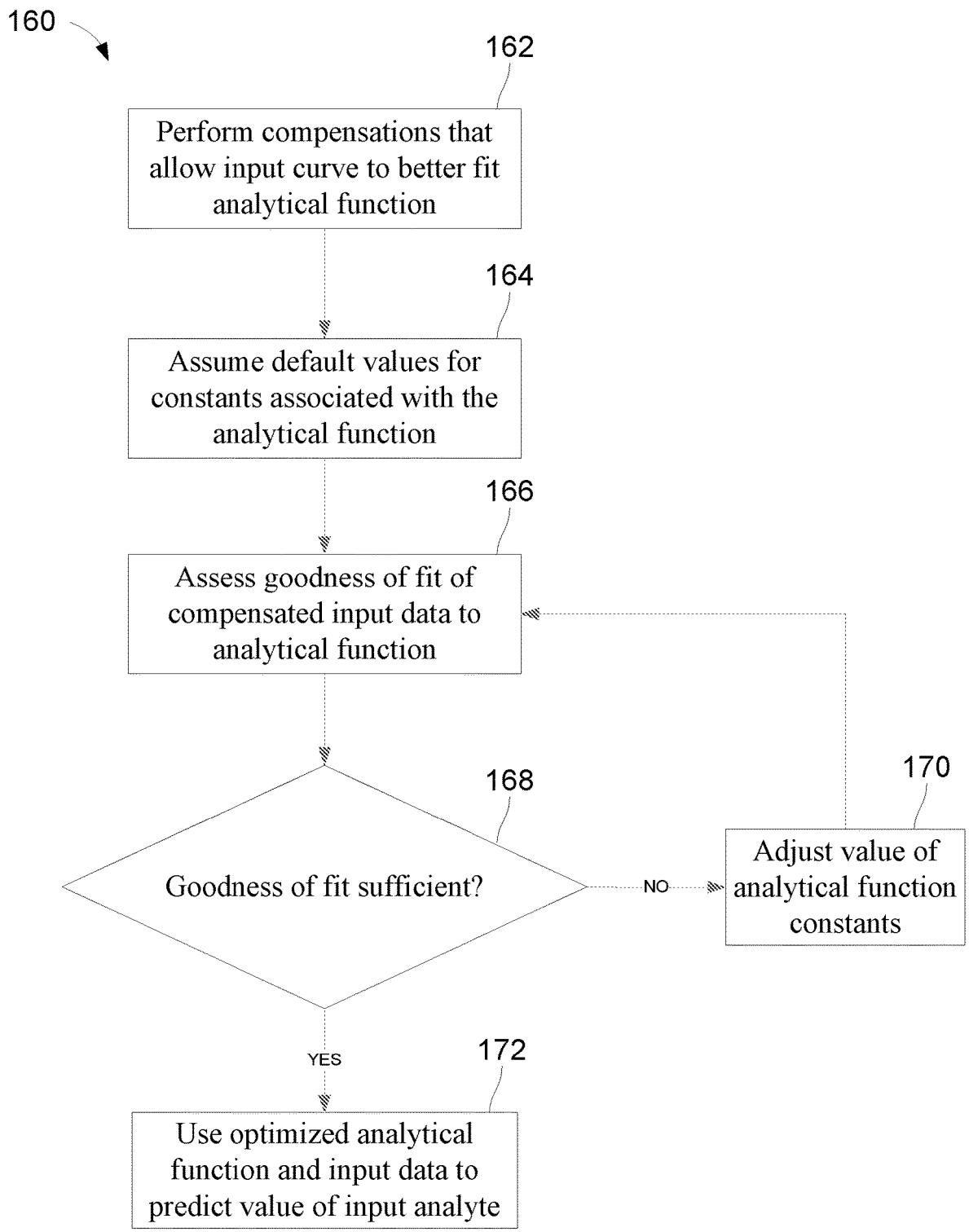
FIG. 14 illustrates a diagram of one method for compensation when the rate of stabilization is not well known for a sensor.

If the rate of stabilization is not sufficiently well known for a sensor but the shape of the calibration curve is known, in particular an exponential settling function of the type $y(t)=y_{terminal}*(1-e^{-t/\tau})$, then the process illustrated in diagram 160 of FIG. 14 may be used. During a calibration test or a field test, any compensations 162 may be performed (heuristical or theoretical) that allow the input curve to better fit a simple analytical time function such as the exponential settling function. For example, the early part of the curve may be adjusted to compensate for diffusion speed to the sensor. Default values may be assumed 164 for constants associated with the analytical time function. In the case of the exponential settling function, a default value for an analytical function time constant tau, $\tau$, may be assumed. The goodness of fit of the (compensated) input data to the analytical function may be assessed 166 and a determination 168 may be made as to whether the good of fit is sufficient. Assuming goodness of fit is insufficient, an adjustment 170 may be made of the value of the analytical function constants, $\tau$, based on the disparity between the input data and analytical function, e.g. overshoot or undershoot and steps 166, 168, 170 may be repeated using an optimizing algorithm (e.g., binary search, executed on the constant tau) to evaluate for the best fit to the analytical function. Once the goodness of fit is sufficient, the optimized analytical function and input data may be used 172 to predict the value of input analyte (CO), e.g., by estimating the terminal value. When performing calibration, this procedure may be used to set the sensitivity ($y_{terminal}/CO_{ppm}$) and when performing a test, this procedure may be used and the terminal value may be divided by the sensitivity to calculate the analyte level.

Compensation in step 162 may be done in either of the following situations. The first situation is when the input breath sample does not immediately propagate to the sensor due to the device geometry but the gas concentration at the sensor surface can be modeled for example by an exponential decay function. The second situation is when a subject's CO level in their breath is not evenly distributed throughout the sample breath, but is actually highest at the end of the exhaled breath. Compensation may be done by adjusting the slope up in the analysis, essentially amplifying the early part of the curve. Several constants that were derived experimentally by optimizing using existing datasets may be utilized.

Over time, the sensors may begin to degrade with repeated use and the calibration data initially used may no longer be valid after some amount of time has passed. Thus, aging data may be used to determine typical behavior over time and also used to compensate the calibration data accordingly. For example, the approximate degradation of certain sensors may be known to be, e.g., 0.6% per month for the first six months and then 0.3% per month thereafter. With this known degradation rate, these parameters may be used to compensate the analysis of each measured value thereafter based upon the amount of time which has elapsed since the device was calibrated.

Figure 15:
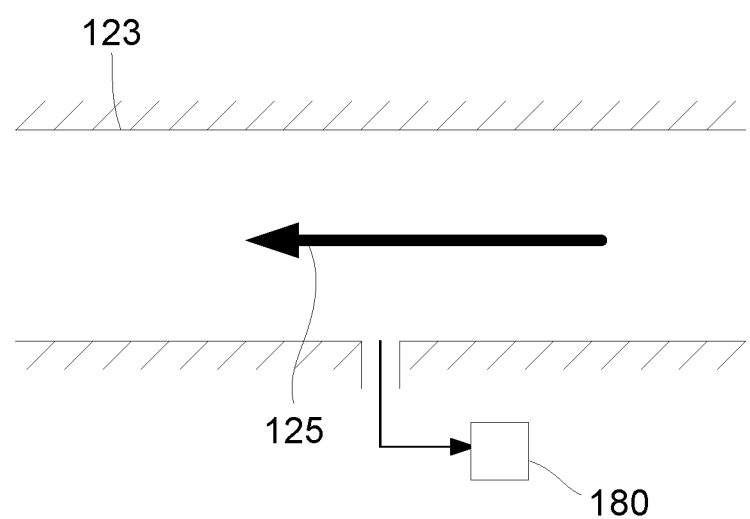
FIG. 15 illustrates an exemplary side view of a sampling unit incorporating an optional spirometer.

In another variation of the sampling unit 20, the device may additionally and/or alternatively incorporate one or more spirometers 180 for monitoring or screening for various conditions, e.g., COPD, asthma, etc. The spirometer 180 may be incorporated into the unit 20 so that it is in fluid communication with a sample breath 125 passing through the flow path 123 to detect and/or monitor parameters, as shown in FIG. 15. The spirometer 180 may be wired to a processor within the unit 20 or it may be wirelessly in communication with the personal electronic device 10 or computer 12. Additionally, the flow path 123 may include a flow switch to increase or decrease flow resistance along the flow path. When the subject breaths into the device, they may be instructed to exhale as vigorously as possible and the device may translate measured pressure into a flow rate to calculate, e.g., forced vital capacity (FVC) or forced expiratory volume, 1 second test (FEV1).

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A method of extrapolating a final value of a parameter from a breath sample, comprising:
    obtaining a calibration curve of a gas having a known parameter concentration;
    recording at least a portion of the calibration curve as a function of time;
    measuring an input response curve of the parameter from the breath sample via a sensor over a period of time;
    associating the input response curve to the calibration curve; and
    extrapolating the final value of the parameter from the breath sample when the breath sample is insufficient to reach a full signal value of the sensor such that the final value is based on the calibration curve associated with the input response curve.

2. The method of claim 1 wherein extrapolating comprises using an iterative method to determine analytical constants to achieve a best fit of an input data to a predetermined function.

3. The method of claim 1 wherein obtaining comprises obtaining the calibration curve of a gas having a known CO concentration.

4. The method of claim 1 wherein measuring comprises measuring over the period of time which is less than a time of obtaining the calibration curve.

5. The method of claim 4 wherein the period of time is less than 15 seconds.

6. The method of claim 1 wherein associating comprises applying an exponential settling function of $y(t)=y_{terminal}*(1-e^{-t/\tau})$, where:
    $\tau$=analytical function time constant
    $y_{terminal}$=a terminal value.

7. The method of claim 1 wherein measuring further comprises measuring the breath sample via at least one CO sensor.

8. The method of claim 7 further comprising measuring the breath sample via at least one $H_2$ sensor.

9. The method of claim 8 further comprising compensating for any $H_2$ measurement sensitivity from the at least one CO sensor with a measurement from the at least one $H_2$ sensor.

\* \* \* \* \*